(12) United States Patent
Reznikoff et al.

(10) Patent No.: US 6,406,896 B1
(45) Date of Patent: Jun. 18, 2002

(54) TRANSPOSASE ENZYME AND METHOD FOR USE

(75) Inventors: William S. Reznikoff; Todd A. Naumann, both of Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/632,021

(22) Filed: Aug. 2, 2000

Related U.S. Application Data (60) Provisional application No. 60/146,686, filed on Aug. 2, 1999.

(51) Int. Cl.⁷ .......................... C12N 9/00; C12N 15/00; C12Q 1/00; C12Q 1/44
(52) U.S. Cl. .......................... 435/183; 435/4; 435/19; 435/440
(58) Field of Search .......................... 435/183, 4, 19, 435/440

(56) References Cited

U.S. PATENT DOCUMENTS

| | | | | |
|---|---|---|---|---|
| 5,925,545 A | * | 7/1999 | Reznikoff et al. | .......... 435/69.2 |
| 5,948,622 A | * | 9/1999 | Reznikoff et al. | .............. 435/6 |
| 5,965,443 A | * | 10/1999 | Reznikoff et al. | .......... 435/473 |
| 6,159,736 A | * | 12/2000 | Reznikoff et al. | .......... 435/455 |
| 6,294,385 B1 | | 9/2001 | Goryshin et al. | ........... 435/450 |

FOREIGN PATENT DOCUMENTS

| WO | WO00/17343 | 3/2000 |
|---|---|---|

OTHER PUBLICATIONS

Stemmer, W. P., "Rapid evolution of a protein in vitro by DNA shuffling," Nature 370:389–391 (1994).
Stemmer, W. P., "DNA shuffling by random fragmentation and reassembly: in vitro recombination for molecular evolution," Proc. Natl. Acad. Sci. U.S.A. 91:10747–10751 (1994).
Ahmed, Asad, "Use of Tranposon–Promoted Deletions in DNA Sequence Analysis", Letter to Editor in J.Mol. Biol., 178:941–948 (1984).
Benjamin, Howard W., "Excision of Tn10 from the donor site during transposition occurs by flush double–strand cleavages at the transposon termini," Proc. Natl. Acad. Sci. USA, 89:4648–4652 May 1992.
Craigie, Robert, et al., "A defined system for the DNA strand–transfer reaction at the initiation of bacteriophage Mu transposition: Protein and DNA substrate requirements," Proc. Natl. Acad. Sci. USA, 82:7570–7574 Nov. 1985.
de la Cruz, Norberto B., et al., "Characterization of the TN5 Transposase and Inhibitor Proteins: a Model for the Inhibition of Transposition," Journal of Bacteriology, 175(21):6932–6938 Nov. 1993.
Delong et al., "Trans–acting Transposase Mutant from Tn5" Proc. Natl. Acad. Sci. USA 88(14):6072–6076 (1991).

Devine et al., "Efficient Integration of Artificial Transposons into Plasmid Target in vitro: a Useful Tool for DNA Mapping, Sequencing and Genetic Analysis", Nucleic Acid Research, 22 No. 18:3765–3772 (1994).
Devine et al., "A Transposon–base Strategy for Sequencing Repetitive DNA in Eukaryotic Genomes", In Press, Genome Research (1998).
Goryshin, et al., "Tn5 in Vitro Transposition," The Journal of Biological Chemistry 273:7367–7374 (1998).
Hattori et al., "A Novel Method for Making Nested Deletions and Its Applications for Sequencing of a 300 kb Region of Human APP Locus", Nucleic Acids Research, 25 No. 9: 1802–1808 (1997).
Henikoff, Steven, "Unidirectional Digestion with Exonuclease III Creates Targeted Breakpoints for DNA Sequencing", Gene, 28: 351–359 (1984).
Jilk et al., "Implications of Tn5–Associated Adjacent Deletions", J. of Bacteriology, 175: 1264–1271 (1993).
Jilk, Ross A., et al., "The Organization of the Outside End of Transposon Tn5," Journal of Bacteriology, 178(6):1671–1679 (03/96).
Johnson et al., "DNA Sequences at the Ends of Transposon Tn5 Required for Transposition", Nature 304(21):280–282 (1983).
Krebs et al., "Use of a Tn5 derivative that creates lacZ translational fusions to obtain a transposition mutant," Gene 63:277–285 (1988).
Krishnan et al., "Construction of a Genomic DNA 'Feature Map' by Sequencing from Nested Deletions: Application to the HLA Class I Region", Nucleic Acids Research, 23 No. 1: 117–122 (1995).
Lavoie, B.D., et al., "Transposition of Phage Mu DNA," Dept. of Biochemistry, U. of Western Ontario.
Mizuuchi, Kiyoshi, "In Vitro Transposition of Bacteriophage Mu: A Biochemical Approach to a Novel Replication Reaction," Cell, 35:785–794 Dec. 1983.
Morisata, Donald, et al., "TN10 Transposition and Circle Formation In Vitro," Cell, 51:101–111 (Oct. 9, 1987).
Naumann et al., "Trans catalysis in Tn5 transposition," PNAS 97:8944–8949 (2000).
Sakai, Janice, et al., "Identification and characterization of a pre–cleavage synaptic complex that is an early intermediate in TN10 transpositon," The EMBO Journal, 14(7):4374–4383 (1995).
Weinreich, Michael D., "A Functional Analysis of the TN5 Transposase: Identification of Domains Required for DNA Binding and Multimerization," J. Mol. Biol., 241:166–177 (1994).

(List continued on next page.)

Primary Examiner—Ponnathapu Achutamurthy
Assistant Examiner—Malgorzata A. Walicka
(74) Attorney, Agent, or Firm—Quarles & Brady LLP (57) ABSTRACT

Modified Tn5 transposase proteins having a preference for transposon Tn5 inside ends rather than outside ends are disclosed and can be used in combination with a transposase enzymes that prefer outside ends to inside ends in a method for end-specific directed transposition in vivo or in vitro.

17 Claims, 6 Drawing Sheets

OTHER PUBLICATIONS

Weinreich, Michael D., et al., "Evidence that the cis preference of the Tn5 transposase is caused by nonproductive multimerization," *Genes & Development,* 8:2363–2374 (1994).

Wiegand et al., "Characterization of Two Hypertransposing Tn5 Mutants", *J. Bacteriol.* 174(4):1229–1239 (1992).

Wiegand et al., "Transposase Mutants That Increase the Transposition Frequency of Tn5", PhD Thesis (Abstract) University of Wisconsin–Madison (1993).

York, et al., "Purification and biochemical analyses of monomeric form of Tn5 transposase," *Nucleic Acids Research* 24:3790–3796 (1996).

York, et al., "DNA binding and phasing analyses of Tn5 transposase and a monomeric variant," *Nucleic Acids Research* 25:2153–2160 (1997).

Zhou et al., "Three Types of Novel Mutations in the NH–2–Terminus of Tn5 Transposase: Structure–function of Transposase", Keystone Symposium on Transposition and Site–Specific Recombination: Mechanism and Biology (Abstract) Jan. 1994, *J. of Cell. Biochem. Suppl.* 0(18B) (1994).

Zhou et al., "Tn5 Tranposase Mutants that Alter DNA Binding Specificity," *J. Mol. Biol.* 271:362–373 (1997).

* cited by examiner

SEQUENCE LISTING

<160> NUMBER OF SEQ ID NOS: 5

<210> SEQ ID NO 1
<211> LENGTH: 1431
<212> TYPE: DNA
<213> ORGANISM: Transposon Tn5
<220> FEATURE:
<221> NAME/KEY: CDS
<222> LOCATION: (1)..(1428)

<400> SEQUENCE: 1

| | | | | | | | | | | | | | | | | |
|---|---|---|---|---|---|---|---|---|---|---|---|---|---|---|---|---|
| atg | ata | act | tct | gct | ctt | cat | cgt | gcg | gcc | g ac | tgg | gct | aaa | tct | gtg | 48 |
| Met | Ile | Thr | Ser | Ala | Leu | His | Arg | Ala | Ala | A sp | Trp | Ala | Lys | Ser | Val | |
| 1 | | | | 5 | | | | | 10 | | | | | 15 | | |
| ttc | tct | tcg | gcg | gcg | ctg | ggt | gat | cct | cgc | c gt | act | gcc | cgc | ttg | gtt | 96 |
| Phe | Ser | Ser | Ala | Ala | Leu | Gly | Asp | Pro | Arg | A rg | Thr | Ala | Arg | Leu | Val | |
| | | | | 20 | | | | | 25 | | | | | 30 | | |
| aac | gtc | gcc | gcc | caa | ttg | gca | aaa | tat | tct | g gt | aaa | tca | ata | acc | atc | 144 |
| Asn | Val | Ala | Ala | Gln | Leu | Ala | Lys | Tyr | Ser | G ly | Lys | Ser | Ile | Thr | Ile | |
| | | | 35 | | | | | 40 | | | | | 45 | | | |
| tca | tca | gag | ggt | agt | gaa | gcc | atg | cag | gaa | g gc | gct | tac | cga | ttt | atc | 192 |
| Ser | Ser | Glu | Gly | Ser | Glu | Ala | Met | Gln | Glu | G ly | Ala | Tyr | Arg | Phe | Ile | |
| | 50 | | | | | 55 | | | | | 60 | | | | | |
| cgc | aat | ccc | aac | gtt | tct | gcc | gag | gcg | atc | a ga | aag | gct | ggc | gcc | atg | 240 |
| Arg | Asn | Pro | Asn | Val | Ser | Ala | Glu | Ala | Ile | A rg | Lys | Ala | Gly | Ala | Met | |
| 65 | | | | | 70 | | | | | 75 | | | | | 80 | |
| caa | aca | gtc | aag | ttg | gct | cag | gag | ttt | ccc | g aa | ctg | ctg | gcc | att | gag | 288 |
| Gln | Thr | Val | Lys | Leu | Ala | Gln | Glu | Phe | Pro | G lu | Leu | Leu | Ala | Ile | Glu | |
| | | | | 85 | | | | | 90 | | | | | 95 | | |
| gac | acc | acc | tct | ttg | agt | tat | cgc | cac | cag | g tc | gcc | gaa | gag | ctt | ggc | 336 |
| Asp | Thr | Thr | Ser | Leu | Ser | Tyr | Arg | His | Gln | V al | Ala | Glu | Glu | Leu | Gly | |
| | | | | 100 | | | | | 105 | | | | | 110 | | |
| aag | ctg | ggc | tct | att | cag | gat | aaa | tcc | cgc | g ga | tgg | tgg | gtt | cac | tcc | 384 |
| Lys | Leu | Gly | Ser | Ile | Gln | Asp | Lys | Ser | Arg | G ly | Trp | Trp | Val | His | Ser | |
| | | | 115 | | | | | 120 | | | | | 125 | | | |
| gtt | ctc | ttg | ctc | gag | gcc | acc | aca | ttc | cgc | a cc | gta | gga | tta | ctg | cat | 432 |
| Val | Leu | Leu | Leu | Glu | Ala | Thr | Thr | Phe | Arg | T hr | Val | Gly | Leu | Leu | His | |
| | 130 | | | | | 135 | | | | | 140 | | | | | |
| cag | gag | tgg | tgg | atg | cgc | ccg | gat | gac | cct | g cc | gat | gcg | gat | gaa | aag | 480 |
| Gln | Glu | Trp | Trp | Met | Arg | Pro | Asp | Asp | Pro | A la | Asp | Ala | Asp | Glu | Lys | |
| 145 | | | | | 150 | | | | | 155 | | | | | 160 | |
| gag | agt | ggc | aaa | tgg | ctg | gca | gcg | gcc | gca | a ct | agc | cgg | tta | cgc | atg | 528 |
| Glu | Ser | Gly | Lys | Trp | Leu | Ala | Ala | Ala | Ala | T hr | Ser | Arg | Leu | Arg | Met | |
| | | | | 165 | | | | | 170 | | | | | 175 | | |
| ggc | agc | atg | atg | agc | aac | gtg | att | gcg | gtc | t gt | gac | cgc | gaa | gcc | gat | 576 |
| Gly | Ser | Met | Met | Ser | Asn | Val | Ile | Ala | Val | C ys | Asp | Arg | Glu | Ala | Asp | |
| | | | | 180 | | | | | 185 | | | | | 190 | | |
| att | cat | gct | tat | ctg | cag | gac | aaa | ctg | gcg | c at | aac | gag | cgc | ttc | gtg | 624 |
| Ile | His | Ala | Tyr | Leu | Gln | Asp | Lys | Leu | Ala | H is | Asn | Glu | Arg | Phe | Val | |
| | | | 195 | | | | | 200 | | | | | 205 | | | |
| gtg | cgc | tcc | aag | cac | cca | cgc | aag | gac | gta | g ag | tct | ggg | ttg | tat | ctg | 672 |
| Val | Arg | Ser | Lys | His | Pro | Arg | Lys | Asp | Val | G lu | Ser | Gly | Leu | Tyr | Leu | |
| | | 210 | | | | | 215 | | | | | 220 | | | | |
| tac | gac | cat | ctg | aag | aac | caa | ccg | gag | ttg | g gt | ggc | tat | cag | atc | agc | 720 |
| Tyr | Asp | His | Leu | Lys | Asn | Gln | Pro | Glu | Leu | G ly | Gly | Tyr | Gln | Ile | Ser | |
| 225 | | | | | 230 | | | | | 235 | | | | | 240 | |
| att | ccg | caa | aag | ggc | gtg | gtg | gat | aaa | cgc | g gt | aaa | cgt | aaa | aat | cga | 768 |
| Ile | Pro | Gln | Lys | Gly | Val | Val | Asp | Lys | Arg | G ly | Lys | Arg | Lys | Asn | Arg | |
| | | | | 245 | | | | | 250 | | | | | 255 | | |

-continued

```
cca gcc cgc aag gcg agc ttg agc ctg cgc a gt ggg cgc atc acg cta     816
Pro Ala Arg Lys Ala Ser Leu Ser Leu Arg S er Gly Arg Ile Thr Leu
        260                 265                 270 aaa cag ggg aat atc acg ctc aac gcg gtg c tg gcc gag gag att aac     864
Lys Gln Gly Asn Ile Thr Leu Asn Ala Val L eu Ala Glu Glu Ile Asn
        275                 280                 285 ccg ccc aag ggt gag acc ccg ttg aaa tgg t tg ttg ctg acc agc gaa     912
Pro Pro Lys Gly Glu Thr Pro Leu Lys Trp L eu Leu Leu Thr Ser Glu
290                 295                 300 ccg gtc gag tcg cta gcc caa gcc ttg cgc g tc atc gac att tat acc     960
Pro Val Glu Ser Leu Ala Gln Ala Leu Arg V al Ile Asp Ile Tyr Thr
305                 310                 315                 320 cat cgc tgg cgg atc gag gag ttc cat aag g ca tgg aaa acc gga gca    1008
His Arg Trp Arg Ile Glu Glu Phe His Lys A la Trp Lys Thr Gly Ala
                325                 330                 335 gga gcc gag agg caa cgc atg gag gag ccg g at aat ctg gag cgg atg    1056
Gly Ala Glu Arg Gln Arg Met Glu Glu Pro A sp Asn Leu Glu Arg Met
        340                 345                 350 gtc tcg atc ctc tcg ttt gtt gcg gtc agg c tg tta cag ctc aga gaa    1104
Val Ser Ile Leu Ser Phe Val Ala Val Arg L eu Leu Gln Leu Arg Glu
        355                 360                 365 agc ttc acg ctg ccg caa gca ctc agg gcg c aa ggg ctg cta aag gaa    1152
Ser Phe Thr Leu Pro Gln Ala Leu Arg Ala G ln Gly Leu Leu Lys Glu
        370                 375                 380 gcg gaa cac gta gaa agc cag tcc gca gaa a cg gtg ctg acc ccg gat    1200
Ala Glu His Val Glu Ser Gln Ser Ala Glu T hr Val Leu Thr Pro Asp
385                 390                 395                 400 gaa tgt cag cta ctg ggc tat ctg gac aag g ga aaa cgc aag cgc aaa    1248
Glu Cys Gln Leu Leu Gly Tyr Leu Asp Lys G ly Lys Arg Lys Arg Lys
                405                 410                 415 gag aaa gca ggt agc ttg cag tgg gct tac a tg gcg ata gct aga ctg    1296
Glu Lys Ala Gly Ser Leu Gln Trp Ala Tyr M et Ala Ile Ala Arg Leu
        420                 425                 430 ggc ggt ttt atg gac agc aag cga acc gga a tt gcc agc tgg ggc gcc    1344
Gly Gly Phe Met Asp Ser Lys Arg Thr Gly I le Ala Ser Trp Gly Ala
        435                 440                 445 ctc tgg gaa ggt tgg gaa gcc ctg caa agt a aa ctg gat ggc ttt ctt    1392
Leu Trp Glu Gly Trp Glu Ala Leu Gln Ser L ys Leu Asp Gly Phe Leu
450                 455                 460 gcc gcc aag gat ctg atg gcg cag ggg atc a ag atc tga                1431
Ala Ala Lys Asp Leu Met Ala Gln Gly Ile L ys Ile
465                 470                 475
```

<210> SEQ ID NO 2
<211> LENGTH: 476
<212> TYPE: PRT
<213> ORGANISM: Transposon Tn5

<400> SEQUENCE: 2

```
Met Ile Thr Ser Ala Leu His Arg Ala A sp Trp Ala Lys Ser Val
 1               5                  10                  15

Phe Ser Ser Ala Ala Leu Gly Asp Pro Arg A rg Thr Ala Arg Leu Val
                20                  25                  30

Asn Val Ala Ala Gln Leu Ala Lys Tyr Ser G ly Lys Ser Ile Thr Ile
            35                  40                  45

Ser Ser Glu Gly Ser Glu Ala Met Gln Glu G ly Ala Tyr Arg Phe Ile
        50                  55                  60

Arg Asn Pro Asn Val Ser Ala Glu Ala Ile A rg Lys Ala Gly Ala Met
65                  70                  75                  80
```

```
Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335

Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
        435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 3
<211> LENGTH: 19
<212> TYPE: DNA
```

```
<213> ORGANISM: Transposon Tn5

<400> SEQUENCE: 3
ctgactctta tacacaagt                                              19

<210> SEQ ID NO 4
<211> LENGTH: 19
<212> TYPE: DNA
<213> ORGANISM: Transposon Tn5

<400> SEQUENCE: 4
ctgtctcttg atcagatct                                              19

<210> SEQ ID NO 5
<211> LENGTH: 19
<212> TYPE: DNA
<213> ORGANISM: Transposon Tn5

<400> SEQUENCE: 5
ctgtctcttg aacagatct                                              19
```

TRANSPOSASE ENZYME AND METHOD FOR USE

CROSS-REFERENCE TO RELATED APPLICATIONS

This application claims the benefit of U.S. provisional patent application No. 60/146,686, filed on Aug. 2, 1999, which is incorporated herein by reference in its entirety.

STATEMENT REGARDING FEDERALLY SPONSORED RESEARCH OR DEVELOPMENT

This invention was made with United States government support awarded by the following agency: NIH, Grant No. GM50692. The United States government has certain rights in this invention.

BACKGROUND OF THE INVENTION

Bacterial transppsons such as Tn5 evolved within the cell by maintaining a low mobility level. While necessary for the transposon to survive, the low mobility level has inhibited the ability of researchers to detail the molecular transposition process and to exploit the transposition process for use, e.g., in the development of new diagnostic and therapeutic resources. Tn5 is a conservative "cut and paste" transposon of the IS4 family (Rezsohazy, R., Hallet, B., Delcour, J., and Mahillon, J, "The IS4 family of insertion sequences: evidence for a conserved transposase motif," Mol Microbiol. 9:1283–1295 (1993)) that encodes a 53 kD transposase protein (Tnp) that is responsible for its movement. The wild-type Tn5 transposase amino acid and nucleic acid sequences are known. Ahmed, A. and Podemski, L. The Revised Sequence of Tn5. Gene 154(1), 129–130(1995), incorporated by reference as if set forth herein in its entirety. A nucleic acid sequence that encodes wild-type Tn5 transposase is attached as SEQ ID NO:1. A polypeptide sequence encoded by SEQ ID NO:1 which corresponds to wild-type Tn5 transposase is attached as SEQ ID NO:2.

Figure 1:
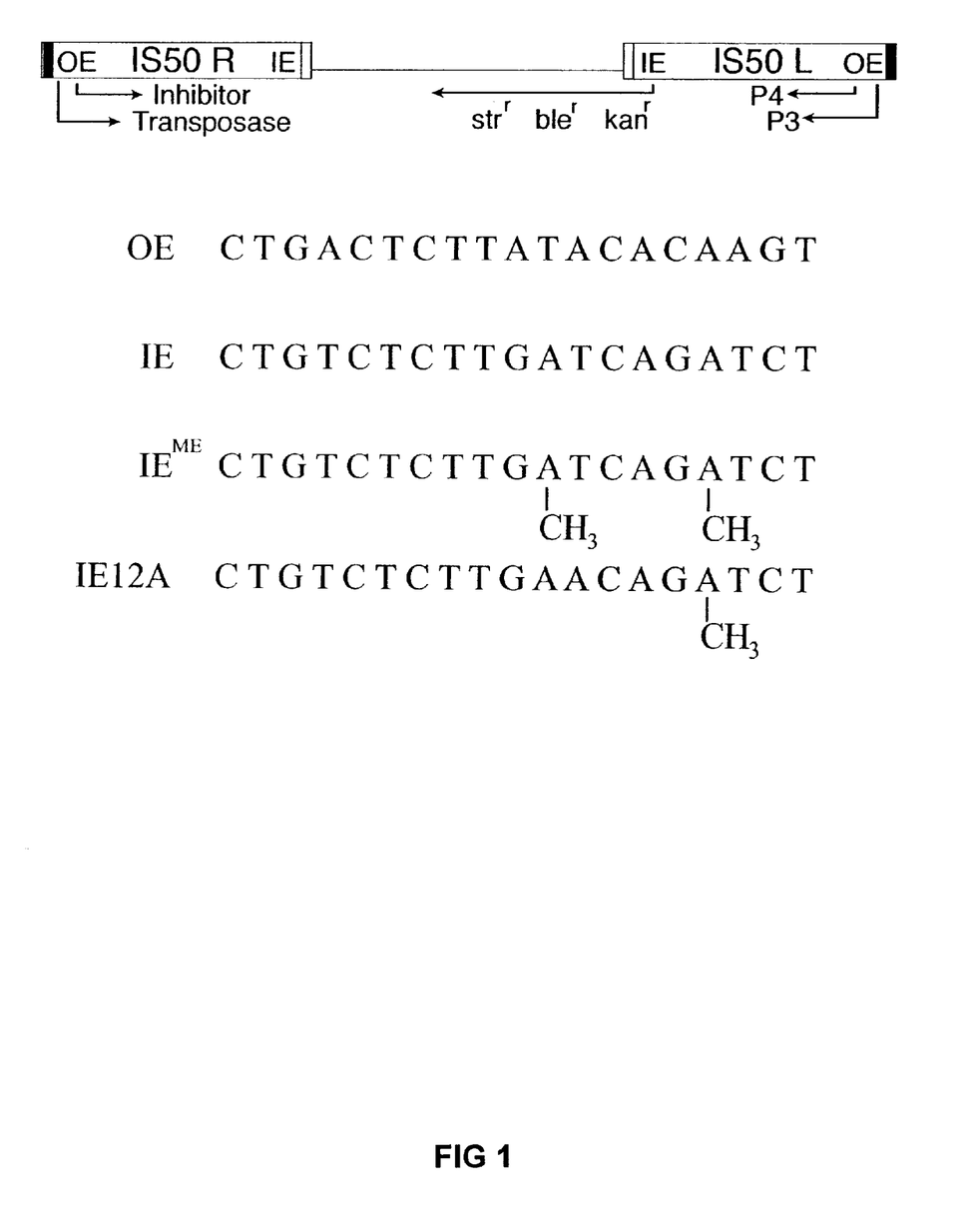
FIG. 1 depicts the structure of Tn5 transposase and the nucleotide sequences of Tn outside ends (OE), inside ends (IE), methylated inside ends ($IE^{ME}$), and modified IE (IE12A).

The Tnp protein facilitates movement of the entire element by binding initially to each of two 19 bp specific binding sequences termed outside end (OE; SEQ ID NO:3), followed by formation of a nucleoprotein structure termed a synapse, blunt ended cleavage of each end, association with a target DNA, and then strand transfer (Rezikoff, W. S., Bhasin, A., Davies, D. R., Goryshin, I. Y., Mahnke, L. A., Naumann, T., Rayment, I., Steiniger-White, M., and Twining, S. S., "Tn5: A molecular window on transposition," Biochem. Biophys. Res. Commun. 266:729–34 (1999)). Tn5 transposase can also promote movement of a single ingertion sequence by using a combination of OE and inside end (IE; SEQ ID NO:4) sequences. The IE is also 19 bp long and is identical to OE at 12 of 19 positions (FIG. 1). In vivo, Tn5 transposase exhibits a marked preference for OE in E. coli. Transposase recognition and binding to IE is inhibited in E. coli by the presence of two dam miethylation sites (CATC palindromes) which add four methyl groups per inside end sequence (IE$^{ME}$; also depicted as SEQ ID NO:4, methylation not shown) (Yin, J. C. P., Krebs, M. P., and Reznikoff, W. S., "Effect of dam Methylation on Tn5 Transpositlion," J. Mol Biol., 199:35–45 (1988), incorporated by reference as if set forth herein in its entirety). This methylation reduces transposition by reducing protein-DNA primary recognition (Jilk, R. A., York, D., and Reznikoff, W. S., "The organization of the outside end of transposon Tn5, " J. Bacteriol. 178:1671–1679 (1996)).

A principal roadblock to understanding how Tn5 transposes is the fact that purified wild-type Tnp has no detectable activity in vitro. Recently, a double mutant hyperactive form of tansposase ("Tnp EK/LP") that promotes all steps of the transposition reaction in vitro was developed. The Tnp EK/LP protein differs from wild-type Tn5 Tnp at position 54 (Glu to Lys mutation) and at position 372 (Leu to Pro mutation), in addition to a non-essential but advantageous change at position 56 that prevents production of a so-called inhibitor protein. The modified hyperactive Tnp protein retains the dramatic preference for OE (or OE-like) termini of wild-type Tn5 transposase. Tnp EK/LP has clarified many aspects of Tn5 transposition that were not previously adequately addressable in vivo.

In vitro polynucleotide transposition is a powerfull tool for introducing random or targeted mutations into a genome, Useful in vitro transposition systems based upon the Tn5 tansposon are disclosed in U.S. Pat. No. 5,925,545 and International Publication No. WO 00/17343, both of which are incorporated herein by reference in their entirety as if set forth herein.

A Tnp protein having an ability to discriminate between IE and OE and having a preference for binding IE is desired to permit directed nucleic acid transposition and to facilitate more complex transposition and genetic engineering strategies of the type disclosed in the above-mentioned patent and application than are available using a Tnp having a single specificity for OE. A Tnp having an enhanced preference for IE$^{ME}$ is also desired because methylation of DNA in common dam+bacterial hosts inhibits binding of existing Tn5 transposases and reduces the ability of existing transposases to facilitate movement of IE-defined transposons.

BRIEF SUMMARY OF THE INVENTION

The present invention is summarized in that a transposase protein modified relative to wild-type Tn5 Tnp as disclosed herein preferentially promotes transposition of a target sequence flanked with wild-type Tn5 transposon inside ends (IE) rather than outside ends (OE) without regard to whether the IE sequences are methylated.

In a related aspect, the present invention is also summarized in that a transposase modified relative to wild-type Tn5 Tnp as disclosed herein has a preference for IE over OE and is hyperactive with regard to transposition frequency.

In another related aspect, the present invention is also summarized in that a transposase modified relative to wild-type Tn5 Tnp as disclosed herein has a preference for IE over OE and catalyzes transposition at a high level even when the IE sequences are methylated. In contrast, wild-type Tn5 transposase does not efficiently recognize methylated IE sequences.

In yet another related aspect, the present invention is summarized in that a transposase according to the invention includes a mutation relative to wild type Tn5 transposase that either (1) alters binding of the transposase to the DNA termini or (2) enhances transposition or (3) both. The mutation can be end-sequence-specific (as in the exemplified embodiments that alter DNA binding) or non-specific (as in the exemplified embodiment that enhances transposition:

In still another related aspect, the present invention is summarized in that a transposase according to the invention has (1) a greater preference for IE than OE and (2) differs from wild-type Tnp in at least one an amino acid selected from the group consisting of amino acid 58, amino acid 344 and amino acid 372.

In still another related aspect, the present invention is summarized in that a transposase according to the invention differs from wild-type Tnp in that it contains at least one of a mutation from glutamic acid to valine at amino acid 58, a mutation from gultamine to lysine at amino acid 344, and a mutation from leucine to gultamine at amino acid 372.

In another related aspect the invention is summarized in that the transposase of the invention can also exhibit a greater preference for IE by reducing the preference for OE. A mutation at amino acid position 8 relative to wild-type transposase can reduce the preference of a transposase for OE, and thereby increase the apparent preference for IE. A mutation from arginine to cysteine can accomplish this modification.

A transposae protein of the invention can promote more transposition of an IE-flanked target sequence in vivo or in vitro than wild-type Tn5 transposase does. A suitable method for determining transposase enzyme activity in vitro is disclosed herein and in U.S. Pat. No. 5,925,545, incorporated herein by reference in its entirety. A suitable method for determining transposase activity in vivo is disclosed herein.

The modified Tn5 Tnp of the present invention differs from wild-type Tn5 Tnp by virtue of at least one change to an amino acid position, where the change is selected from the group consisting of (1) a change at amino acid position 58 that reduces or eliminates a negative interaction between the Tnp and a methylated DNA residue and (2) a change at amino acid position 344 that alters DNA binding. In addition to the changes noted herein, the modified Tnp's of the invention can also include a change at position 56 (such as a Met to Ala change) that prevents production of the so-called inhibitor protein that interferes with transposition. Moreover, the mutant Tn5 transposase proteins can contain mutations in addition to those noted above. Additional mutations relative to the wild-type Tn5 Tnp are disclosed below. The effect of each mutation is disclosed below and it is understood that the applicants have identified amino acid residues of the protein that have a direct impact upon function and that other modifications at the same positions can have effects comparable to, greater than or lesser than those noted on the preference of the protein for inside ends. The wild-type Tn5 trmsposase amino acid sequence is presented in the Sequence Listing. Exemplified changes relative to that wild-type transposase are presented in the text of this application.

The invention is further summarized in that the enzymes disclosed herein facilitate a simple, in vitro system and method for introducing any transposable element from a donor DNA into a target DNA when the transposable element DNA is flanked on either side by IE termini inverted relative to one another. Few other requirements on either the donor DNA or the target DNA are envisioned. It is thought that Tn5 has few, if any, preferences for insertion sites, so it is possible to use the system to introduce desired sequences at random into target DNA. Therefore, it is believed that this system and method, employing the modified transposase described herein and a simple donor DNA, is broadly applicable to introduce changes into any target DNA, without regard to its nucleotide sequence. It will, thus, be applied to many problems of interest to those skilled in the art of molecular biology.

Finally, although the changes noted herein are disclosed in terms of changes at the protein level, it is well within the ability of a skilled artisan to modify a polynucteotide that encodes a Tn5 transposase protein to encode the modified proteins of the invention. The skilled artisan also understands the degeneracy of the genetic code and understands that a plurality of codons can direct the production of a single amino acid residue.

The invention will be more fully understood upon consideration of the following detailed description taken in conjunction with the accompanying drawings.

DETAILED DESCRIPTION OF THE PREFERRED EMBODIMENTS

Random mutagenesis studies performed on the Tnp gene have demonstrated that it is possible to isolate mutations in the protein that increase the rate of transposition (Krebs and Reznikoff, 1988; DeLong, A., and Syvanen, M., "Trans-acting transposase mutant from Tn5," *P.N,A.S U.S.A.* 88;6072–6 (1991); Wiegand, T. W., and Reznikof, W. S., "Characterization of two hypertransposing Tn5 mutants," *J. Bacteriol.* 174:1229–1239 (1992); Weinreich, M. D., Gasch, A., & Rezuikoff, W. S., "Evidence that the cis preference of the Tn5 transposase is caused by nonproductive multimerization," *Genes. Dev.* 8: 2363–2374 (1994); Zhou, M., & Reznikoff, W. S., "Tn5 mutants that alter DNA binding specificity," *J. Mol. Biol.* 271:362–73. (1997), incorporated by reference as if set forth herein in its entirety). This makes transposase unique in comparison to most enzymatic proteins that appear to have evolved for maximum in vivo activity. This is likely due to the fact that high rates of transposition would be detrimental to the survival of the transposon and hence transposase has evolved to have an 'optimal' level that is much lower than its maximum attainable level.

Applicants have isolated a set of related mutant transposase proteins that differ from wild type Tn5 transposase in that the mutant proteins show a preference in a transposition system for inside ends (IE), and in some cases, methylated inside ends ($IE^{ME}$), rather than for outside ends (OE), which are unmethylated because they lack a methylation site. The end preference of a mutant transposase can characterized either (1) by the in vivo transposition frequency observed when it is used in a system in which the target polynucleotide is flanked with either OE and $IE^{ME}$ termini, or (2) by the ratio of the in vivo transposition frequencies observed when it is used in a pair of systems in which the target polynucleotide is flanked with OE and $IE^{ME}$ terini, respectively. Although applicants have exemplified a number of transposase proteins differing from wild-type Tn5 Tnp at one, four, five, and seven mutations, one can reasonably predict from their analysis the effects of particular individual mutations.

EXAMPLE

Overview

A number of related methods were used to obtain the family of mutants disclosed herein. In a first method, the applicants obtained mutants that restored in vivo transposition activity to a mutated end binding sequence that is not recognized as a substrate by wild type transposase. In a second method, the applicants introduced directed mutations into certain products of the first method to determine the preferred structure of a mutant transposase according to the invention.

In the first method, the mutant IE end binding sequence contains an adenine in place of thymine at position 12 ("IE12A"; SEQ ID NO:5). The thymine-to-adenine change in IE12A destroys one of the two methylation sites of wild-type IE. Applicants used sPCR, a combinatorial, random directed mutagenesis technique to obtain modified transposase proteins that can restore transposition activity to polynucleotides flanked with IE12A. sPCR was developed and described gtemmer, W. P., "Rapid evolution of a protein in vitro by DNA shuffling," *Nature* 370:389–391 (1994) and Stemmer, W. P., "DNA shuffling by random fragmentation and reassembly: in vitro recombination for molecular evolution," *Proc. Natl. Acad. Sci. U.S.A.* 91:10747–10751 (1994), both of which are incorporated by reference herein as if set forth in their entirety. Briefly, DNA is manipulated in vitro in the SPCR method to introduce point mutations and to allow random recombination within a population of mutant sequences. The mutated genes can be cloned into plasmids which can be selected for increased activity in vivo. Clones having desirable phenotypes are then used as substrates for subsequent rounds of mutagenesis/ recombination and selection for a further improved phenotype.

The sPCR method can be used in conjunction with a screen (instead of a selection) in which a modest number of colonies (~$10^4$) are analyzed per round (Crameri, A., Whitehoin, E. A., and Stemmer, W. P., "Improved green fluorescent protein by molecular evolution using DNA shuffling," Nat. *Biotechnol.* 14:315–319 (1996), and Zhang,. J. H., Dawes, G., and Stemmer, W. P., "Directed evolution of a fucosidase from a galactosidase by DNA shuffling and screening," *Proc. Natl. Acad. Sci. U.S.A.* 94, 4504–4509 (1997), both of which are incorporated by reference herein as if set forth in their entirety. A papillatlon assay described in the Example that follows was used as a screen for transposase mutants that restore transposition activity to polynucleotides flanked with IE12A. The papillation assay is a modification of the assay described by Krebs, M. P., and Reznikoff, W. S., "Use of a Tn5 derivative that creates lacZ translational fusions to obtain a transposition mutant," *Gene* 63:277–85 (1988), incorporated by reference in its entirety as if set forth herein. In the papillation assay, productive transposition in frame into an actively expressed gene results in formation of a β-Gal fusion protein. These cells turn blue (due to presence of X-gal) and grow at an increased rate within the colony (lactose utilization). The rate at which these papillae form can be used to compare transposition rates promoted by mutated proteins.

The applicants determined the ability of mutant transposases identified using the first method to catalyze in vivo transposition of polynucleotides flanked either with wild-type OE or with wild-type IE in a dam- strain (i.e., the nucleic acid was umnethylated). Among the mutants identified using the method, applicants identified a mutant transposase ("Tnp sC7") that retained near-wild-type activity with OE-flanked polynucleotides but which had very high activity with IE-flanked polynucleotides and even higher activity with IE-flanked polynucleotides when tested in a dam+ strain (i.e., the nucleic acid was methylated, subsequently "$IE^{ME}$"). Tnp sC7 contains seven mutations relative to wild-type transposase.

In the second method, it was subsequently determined that a related mutant transposase ("Tnp sC7v2.0") having only four of the seven mutations of Tnp sC7 exhibited a still higher IEB:OE activity ratio. Both Tnp sC7 and Tnp sC7v2.0 contain a mutation that inhibits OE related activity (R8C), two mutations that specifically increase $IE^{ME}$ related activity (E58V, E344K), and a mutation that increases transposition of polynucleotides flanked by either $IE^{ME}$ or OE (L372Q).

Obtaining the Mutant Tnp's

Figure 2:
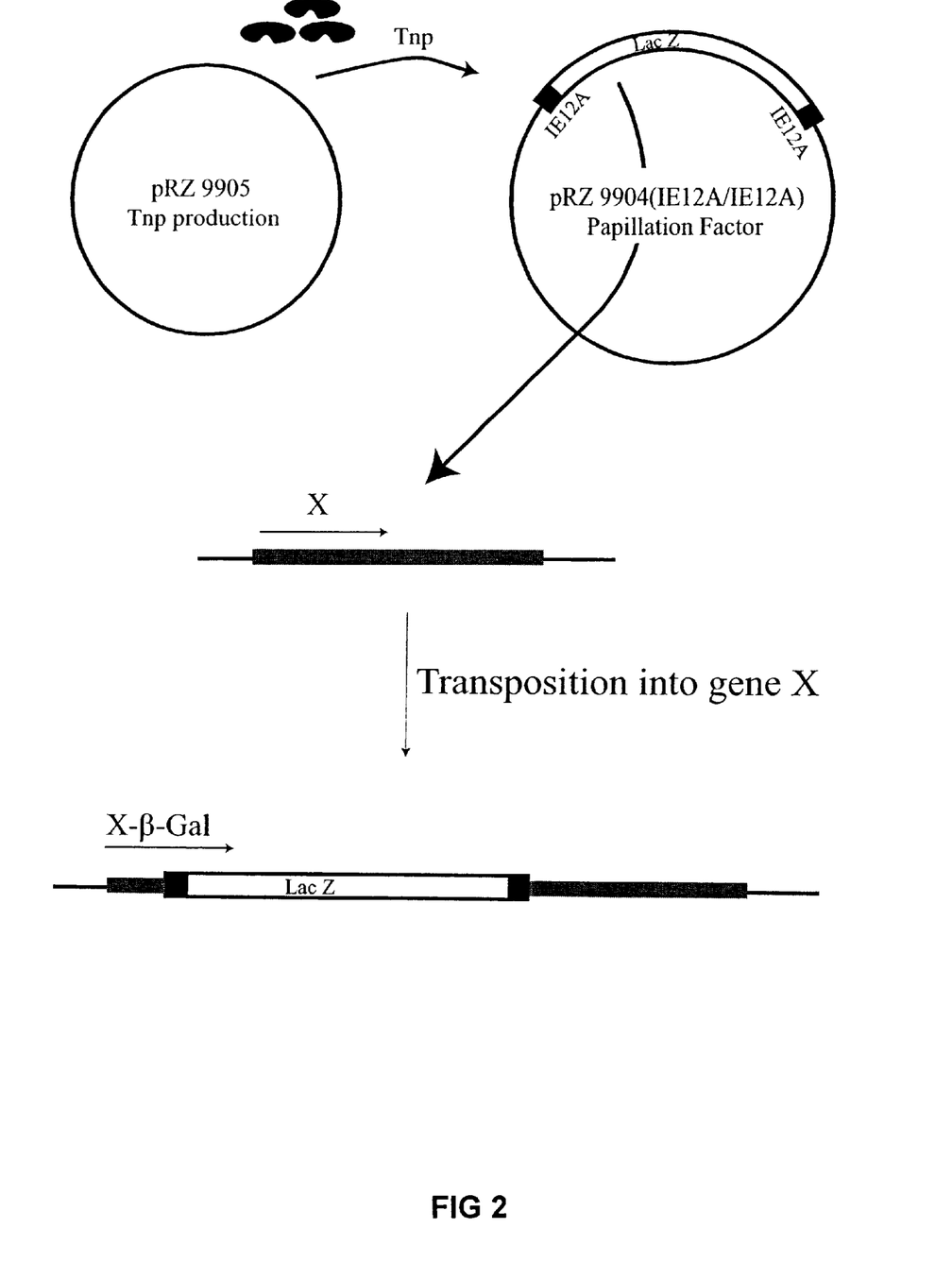
FIG. 2 is a schematic depiction of the molecular basis for a papillation assay for observing transposition in vivo.

The modified papillation assay used to screen for productive transposition is shown and described in FIG. 2. In a first plasmid ("pRZ9904 (IE12A/IE12A)") used, a pair of inverted IE12A termini flank a polynucleotide that contains a lacZ gene but which lacks both a promoter and a translational start site. A second plasmid ("pRZ9905") used in the assay, encodes for transposase that can move the lacZ-containing polynucleotide. Plasmids having these attributes can readily be constructed by a skilled artisan. Materials and methods are detailed below.

Five random mutants that suppressed the end sequence mutation and yielded papillae were: solated after an initial cycle of mutagenesis/recombination. Equal amounts of plasmid encoding each of these mutant transposases were then used as the initial substrates for a second round of mutagenesis/recombination. Following this second round, the mutated transposase genes were cloned into vector DNA and screened a second time for transposition activity with IE12A-defamed polynucleotides via the papillation screen. From this second round, a total of 6 active mutants were isolated. A third round of mutagenesis/recombination was then performed followed by screening for activity with the mutant end sequence. This time hundreds of colonies were positive for papillation. Of these, 7 were clearly more active than the others and were isolated to serve as a template for a fourth round. In the fourth round of screening there were hundreds of transposing colonies visualized during the screening process. None of these, however, were as active as the most active mutant from the third round of mutagenesis/recombination (Tnp sC6).

Figure 3A:
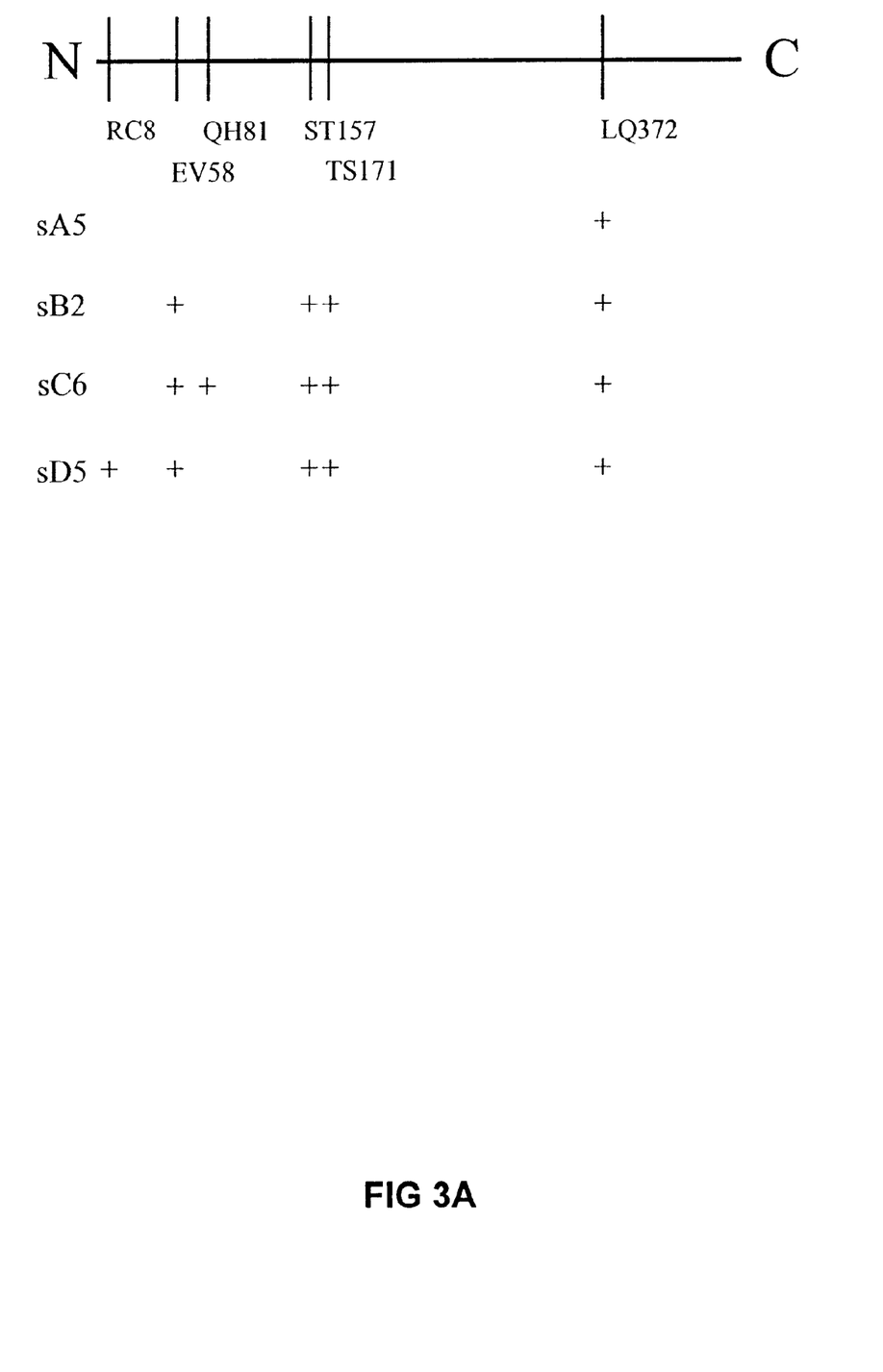
FIG. 3A depicts the locations of mutations observed in four successive rounds (A, B, C, D) of mutagenesis/recombination.
Figure 3B:
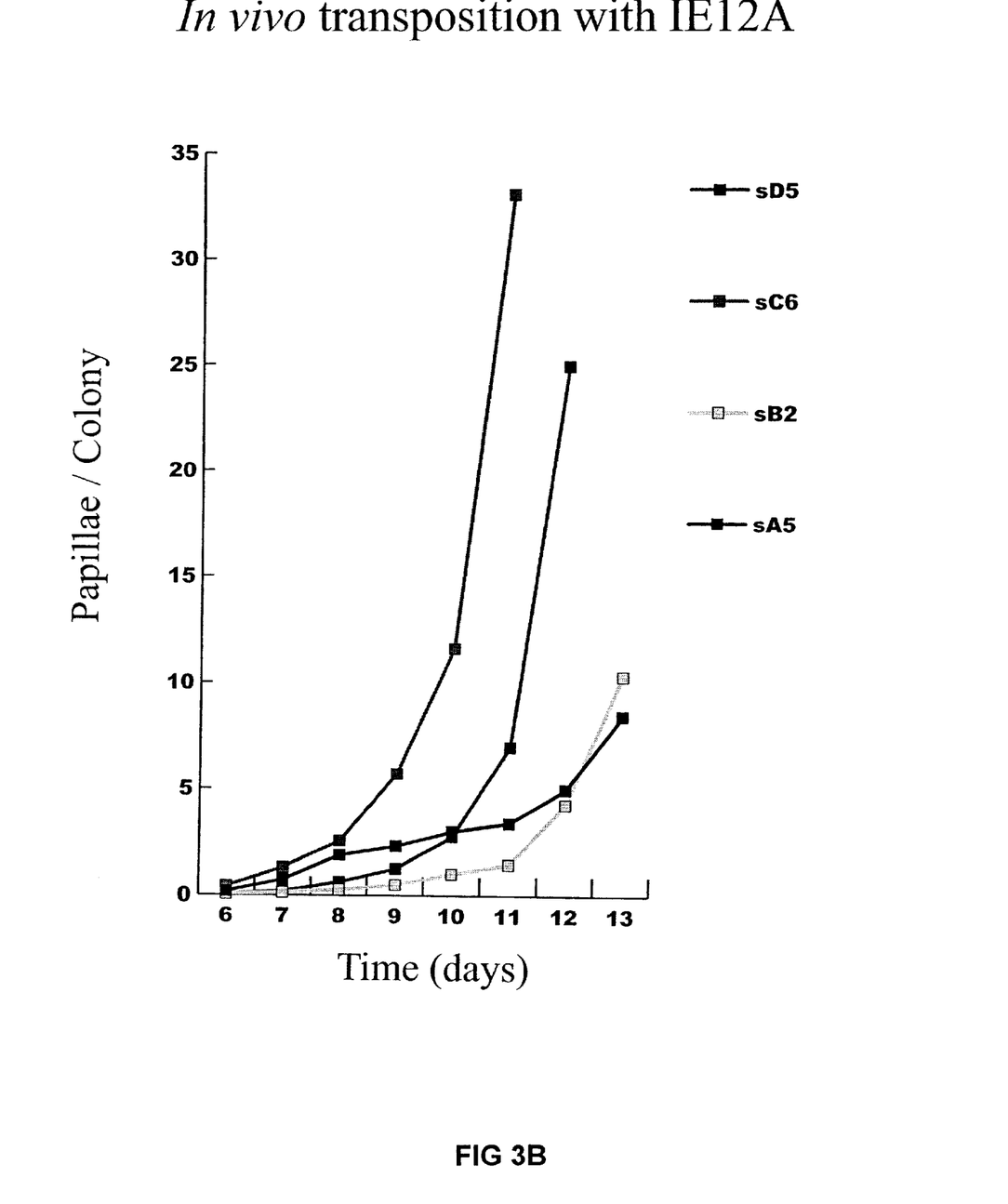
FIG. 3B depicts the in vivo transposition profile of each of the mutants of FIG. 3A.

The most active isolate from each round was sequenced and tested for transposition activity with IE12A defined transposons in a quantitative papillation assay (see FIGS. 3A and 3B). FIG. 3A depicts the mutations relative to wild-type Tnp of Tnp sA5 (best first round papillator), sB2 (best second round papillator), sC6 (best third round papillator), and sD5 (best fourth round papillator). FIG. 3B depicts the transposition activities of the four isolates in vivo in the papillation assay. Tnp WT was also tested but failed to promote a single detectable transposition event. The mutation Q81H is the only mutation that distinguishes the most active mutant, sC6, isolated in the third round, from the noticeably less active mutant sB2, isolated in the second round. A second isolate from the third round, Tnp sC7, is similar to the fourth round isolate sD5, except that it has two additional mutations (D217A and E344K). Tnp sC7's activity with IE12A defined transposons is similar to that of the fourth round isolate sD5 (data not shown).

The Mutant Tnp's can Promote Transposition of OE- and IE-defined Transposons The mutant Tnp's described above were of initial interest because they could restore transposition activity to transposons flanked with IE12A termini that are inactive in the presence of wild-type Tnp. Although the transposase mutants functioned increasingly well with these transposons, the transposition rate did not approach the level of activity that is required in vitro. In fact, the in vivo activity of Tnp sC6 with IE12A ends only restored activity to a level similar to that of Tnp WT with transposons defined by OE (data not shown).

Figure 4:
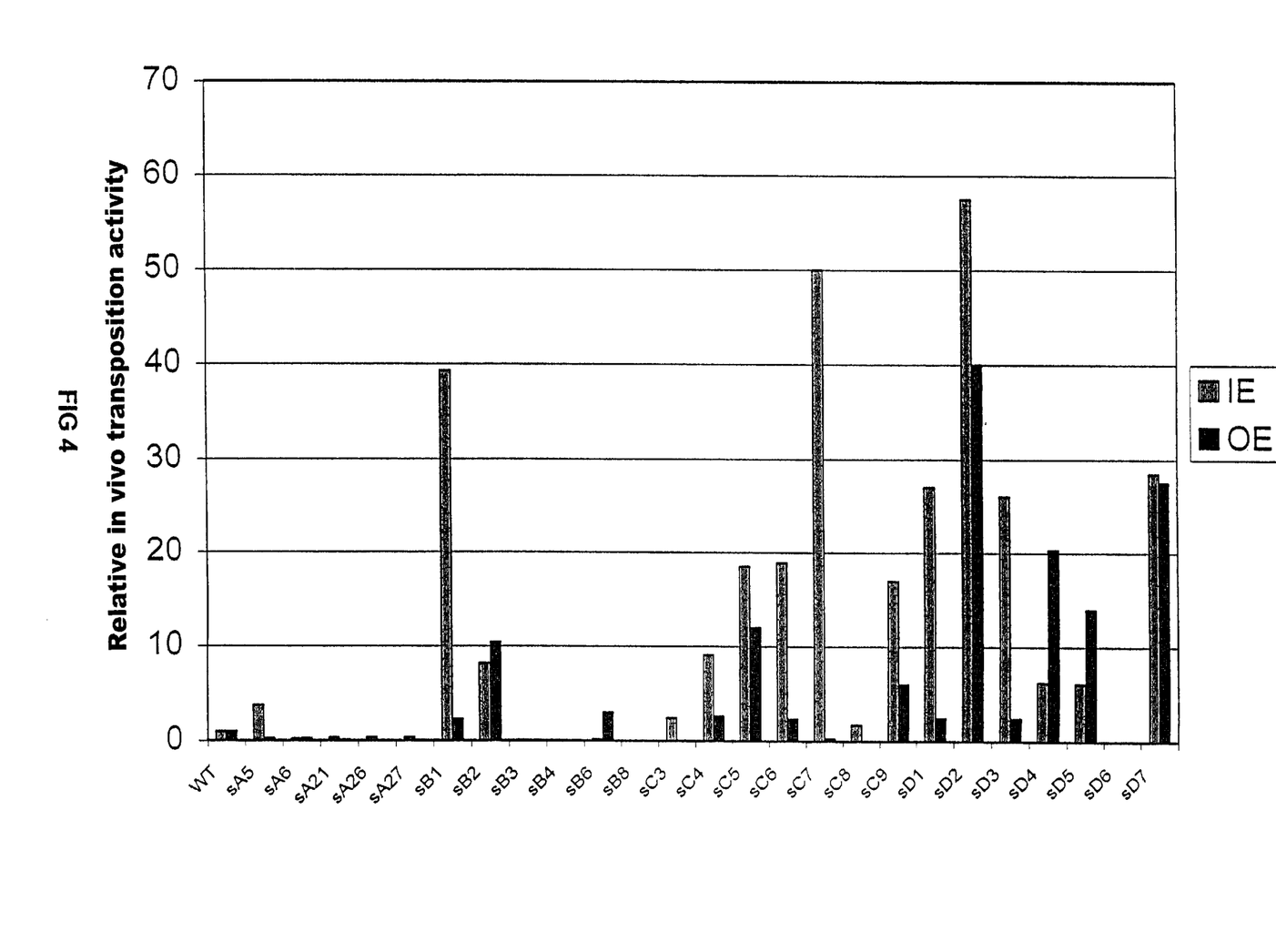
FIG. 4 depicts the relative preference of mutant transposases obtained in successive rounds of mutagenesis/recombination for OE and IE in a dam- strain of E. coli.

Interestingly, however, most of the isolated mutants were hyperactive with transposons defined by at least one of the native end sequences (IE or OE). These transposition preferences were determined in a dam− (DNA unmethylated) strain using the mating out assay of Goryshin, I. Y., Kil, Y. V., and Rezrikoff, W. S., "DNA length, and twisting constraints on IS50 transposition," *Proc Natl Acad Sci U S A* 91:10834–10838 (1994), incorporated by reference as if set forth herein in its entirety, FIG. 4 depicts the in vivo transposition activity of 25 mutant Tnps with IE and OE defined transposons in the mating-out assay in a dam− strain, normalized to the activity of wild-type Tnp ($6.5 \times 10^{-5}$ normalized to 1). In this assay in a dam− environment, Tnp WT shows generally equivalent activity levels whether the substrate polynucleotide is flanked with IE or with OE. On the other hand, many of the mutants, exhibited higher activity with IE than with OE. This is not surprising, since the mutants were obtained in a screen using IE12A, which differs from IE at only 1 nucleotide. In contrast, OE differs from IE12A at 6 nucleotides. One mutant in particular, Tnp sC7, displayed a very interesting phenotype. It is markedly hyperactive with IE transposons while exhibiting little change in the frequency of OE transposon movement. The ability to discriminate between IE and OE is important because it facilitates multi-part transpositions that separately employ IE and OF ends, where a reaction can be directed one way or another by providing a transposase that prefers either IE or OE. A preference for IE over OE of greater than about 5-fold may be suitable, though a preference of greater than about 10-fold for IE is more preferred. A preference of greater than about 20-fold is still more preferred. FIG. 4 demonstrates that a skilled artisan can obtain such mutant transposases using the methods disclosed herein. In particular, mutants sB 1, sC6, sC7, sD1 and sD3 are examples of such mutants.

Even more significantly, however, Tnp sC7 is not only not inhibited for transposition activity by methylated IE (which reduces Tnp WT levels by ~102) but actually prefers $IE^{ME}$ transposons to those flanked by IE, as is shown in the mating out results of Table 1 which indicate that transposition frequency with OE is reduced m a dam+ strain for both Tnp sC7 and Tnp WT. Since binding of Tnp to OE is not affected by dam methylation, this difference merely reflects the difference in transposition activity between dam+ strains and dam− strains. Despite this reduction, the rate of IE defined transposition facilitated by Tnp sC7 is even higher in the dam+ strain due to the presence of methylation in the ends. In contrast, methylation of the end sequence inhibits recognition by wild-type transposase. On the basis of its ability to discriminate between IR and OE, and because of its insensitivity to methylation of IE, subsequent attention was directed to Tnp sC7.

TABLE 1

In vivo transposition rate of Tnp WT and Tnp sC7.

| | JCM101 (dam−) | | IE/ | RZ212 (dam+) | | |
|---|---|---|---|---|---|---|
| | IE freq. | OE freq. | OE | $IE^{ME}$ freq. | OE freq. | $IE^{ME}$/OE |
| Tnp WT | $6.5 \times 10^{-5}$ | $6.5 \times 10^{-5}$ | 1.0 | $1.0 \times 10^{-8}$ | $3.1 \times 10^{-6}$ | $3.2 \times 10^{-3}$ |
| Tnp sC7 | $1.8 \times 10^{-3}$ | $3.7 \times 10^{-5}$ | 50 | $2.6 \times 10^{-3}$ | $3.3 \times 10^{-6}$ | 794 |

The role of the individual Tnp sC7 mutations in transposition activity

To understand how individual mutations affect the activity of the protein and in an effort to maximize the activity of the protein and its ability to discriminate between $IE^{ME}$ and OE, the applicants strategically prepared more variant transposases using information obtained from sC7, which as noted above, contained seven mutations relative to wild type transposase. Since a comprehensive trial of all possible combinations of these seven mutations was cumbersome (128 possible combinations) two classes of seven mutants each were engineered. In each mutant of file first class, a unique mutation from sC7 was engineered to revert to wild-type at that position. This set of so-called "minus one" mutant transposases included all possible mutants having 6 of the 7 mutations. In each mutant of the second class, wild-type transposase was engineered to contain exactly one of the 7 mutations from sC7. The get of so-called "plus one" mutant transposases included all possible mutants having only 1 of the 7 mutations. These mutant proteins were all assayed for in vivo transposition activity with $IE^{ME}$ and OE by mating out assays. The results of the analysis are shown in Table 2.

TABLE 2

Results of 'minus ones/plus ones' analysis.

| | 'minus one' $IE^{ME}$ | | 'minus one' OE | | 'plus one' $IE^{ME}$ | | 'plus one' OE | |
|---|---|---|---|---|---|---|---|---|
| | freq. | norm. | freq. | norm. | freq. | norm. | freq. | norm. |
| Wild-type | | | | | $1.0 \times 10^{-8}$ | 1.0 | $3.1 \times 10^{-6}$ | 1.0 |
| sC7 | $2.6 \times 10^{-3}$ | 1.0 | $3.3 \times 10^{-5}$ | 1.0 | | | | |
| RC8C | $3.1 \times 10^{-3}$ | 1.2 | $6.0 \times 10^{-6}$ | 1.8 | — | — | $4.0 \times 10^{-7}$ | 0.1 |
| E58V | $1.8 \times 10^{-6}$ | $6.9 \times 10^{-4}$ | $1.1 \times 10^{-6}$ | 0.3 | $4.0 \times 10^{-4}$ | $4 \times 10^{4}$ | $1.4 \times 10^{-6}$ | 0.5 |
| A157T | $3.1 \times 10^{-3}$ | 1.2 | $4 \times 10^{-6}$ | 1.2 | — | — | $6.6 \times 10^{-7}$ | 0.2 |
| T171S | $2.8 \times 10^{-3}$ | 1.1 | $2.6 \times 10^{-6}$ | 0.8 | $5.6 \times 10^{-9}$ | 0.6 | $1.8 \times 10^{-6}$ | 0.6 |
| D217A | $3.7 \times 10^{-3}$ | 1.3 | $4.5 \times 10^{-6}$ | 1.4 | — | — | $3.4 \times 10^{-6}$ | 1.1 |

TABLE 2-continued

Results of 'minus ones/plus ones' analysis.

| | 'minus one' $IE^{ME}$ | | 'minus one' OE | | 'plus one' $IE^{ME}$ | | 'plus one' OE | |
|---|---|---|---|---|---|---|---|---|
| | freq. | norm. | freq. | norm. | freq. | norm. | freq. | norm. |
| E344K | $5.5 \times 10^{-4}$ | 0.2 | $1.7 \times 10^{-5}$ | 5.2 | $4.3 \times 10^{-8}$ | 4.3 | $6.8 \times 10^{-7}$ | 0.2 |
| L372Q | $2.6 \times 10^{-4}$ | 0.1 | $2.8 \times 10^{-7}$ | 0.1 | $8.9 \times 10^{-8}$ | 8.9 | $1.1 \times 10^{-5}$ | 3.5 | a. 'Minus ones' contain all mutations present in Tnp sC7 except at indicated position. e.g. R8C 'minus one' contains the wild-type argenine at position 8.
b. 'Plus ones' are Tnp WT except that the indicated amino acid is mutated to the residue present in Tnp sC7. e.g. R8C 'plus one' contains a cysteine at amino acid 8.

Sequence-specific mutations. The mutation E58V has the most profound effect of all the mutations on the activity of Tnp sC7. This mutation in the wild-type background (E58V 'plus one') increases $IE^{ME}$ related transposition by 40,000 fold while removal of the mutation from Tnp sC7 (E58V 'minus one') drops the total activity by more than 1,000 fold. The mutation has comparatively little effect on OE related activity.

The mutation E344K exhibits a similar, though much weaker, sequence specific effect on activity. When removed from Tnp sC7 (E344K 'minus one'), $IE^{ME}$ related activity decreases by 5 fold while OE related activity is stimulated about 5 fold. This result is mirrored in the 'plus ones' data as E344K in the wild type background stimulates $IE^{ME}$ related activity 4 fold and decreases OE related activity about 5 fold.

Non-sequence-specific mutations. The mutation L372Q strongly stimulates Tnp sC7 activity with $IE^{ME}$. When removed from sC7 both $IE^{ME}$ and OE related activity are reduced to the same degree. When added to wild-type transposase, its 'plug one' phenotype stimulates activity with both substrates.

Other mutations. The mutation R8C was the most interesting of the remaining four mutations. When the mutation is added to wild-type transposase, OE related transposition was reduced nearly 10 fold. When the mutation was removed from sC7 OE related activity increased approximately 2 fold. In a methylating host, its removal from sC7 had little effect on $IE^{ME}$ related activity while by itself it decreased $IE^{ME}$ related activity to below detectable levels. None of the remaining three (A157T, T171S, D217A) mutations has much effect on either $IE^{ME}$ or OP related activity when removed from sC7. To determine whether any combination of these mutations would lead to an increase in overall $IE^{ME}$ related activity without sacrificing its specificity for $IE^{ME}$ over OE, the applicants engineered pairwise reversions of sC7 at these positions as well as a triple-reversion mutant. The construct with all three of these mutations reverted had the second highest $IE^{ME}$ related activity and the best ability to discriminate between $IE^{ME}$ and OE (Table 3). This four-mutant construct, Tnp (R8C, E58V, E344K, L372Q), was renamed Tnp sC7 v2.0.

TABLE 3

In vivo frequency of Tnp sC7 with indicated mutations reverted to wild type.
Numbers in parenthesis indicate positions changed to wild-type.

| | $IE^{ME}$ | | OE | | $IE^{ME}$/ |
|---|---|---|---|---|---|
| | freq. | norm. | freq. | norm. | OE |
| Tnp sC7 | $2.6 \times 10^{-3}$ | 1.0 | $3.3 \times 10^{-6}$ | 1.0 | 794 |
| Tnp sC7(157,171) | $6.5 \times 10^{-3}$ | 2.5 | $7.0 \times 10^{-6}$ | 2.1 | 933 |
| Tnp sC7(157,217) | $8.4 \times 10^{-3}$ | 3.3 | $2.25 \times 10^{-5}$ | 6.8 | 373 |
| Tnp sC7(171,217) | $5.8 \times 10^{-3}$ | 2.3 | $1.18 \times 10^{-5}$ | 3.6 | 502 |
| Tnp sC7(157,171,217)α | $7.4 \times 10^{-3}$ | 2.8 | $7.1 \times 10^{-6}$ | 2.1 | 1042 |

α Re-named sC7v2.0.
Abbreviations:
OE = outside end
IE = inside end
$IE^{ME}$ = dam methylated inside end Tnp sC7 is less than the sum of its individual mutations. The Tnp E58V (E58V 'plus one') mutant has an activity increase of $4 \times 10^4$ over Tnp WT alone. The composite mutant with E58V removed (E58V 'minus one') has an increase of $1.8 \times 10^2$ over Tnp WT. Additivity would then predict that Tnp sC7 would have an activity increase of:

$$(4 \times 10^4)(1.8 \times 10^2)\ 7.2 \times 10^6$$

However the stimulation of the composite mutation is actually much lower ($2 \times 10^5$). In other words the increase obtained by adding E58V to the other 6 mutations is $1.1 \times 10^3$ fold, and not the $4 \times 10^4$ fold gtimulation seen by adding E58V into the wild-type background. This may be because that E58V and E344K are both stimulating the same step (primary DNA binding) and are less than additive when combined.

Tnp sC7v2.0 effectively transposes $IE^{ME}$ defined transposons in vitro

Figure 5A:
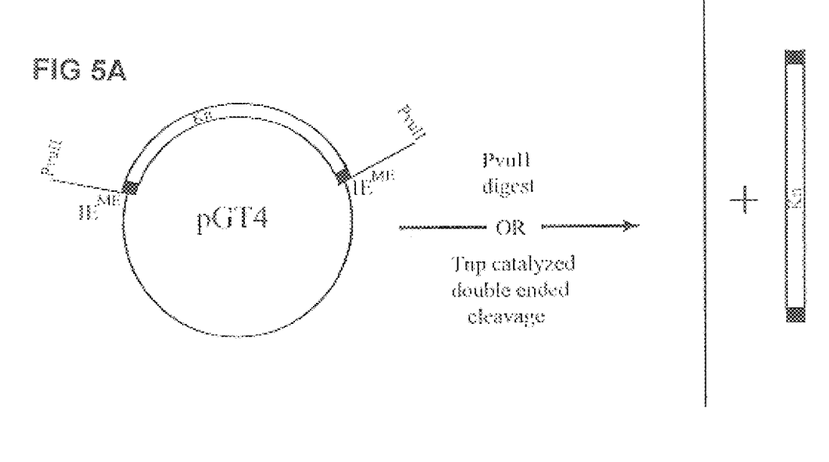
FIG. 5A depicts a plasmid suitable for use in an in vitro transposition method.

The ability of Tnp sC7v2.0 to promote transposition of $IE^{ME}$ defined transposons in vitro was tested under the same conditions developed for movement of OE defined transposons by Tnp EK/LP (Coryshin, I. Y., and Reznikoff, W. S., "Tn5 in vitro transposition," *J. Biol. Chem.* 273:7367–7374 (1998), incorporated by reference as if set forth herein in its entirety). Substrate plasmid pGT4, a high-copy number pUC19-based vector in which inverted $IE^{ME}$ end sequences flank a kanamycin resistance gene, was purified as a super-coiled monomer (see Materials and Methods). This plasmid was constructed so that digestion with PvuII restriction endonuclease causes release of the transposon from the donor backbone DNA (see FIG. 5A). Tnp sC7v2.0 was produced and purified by cloning the nucleotide sequence in an expression vector, expressing the protein in a host cell and isolating the protein from an extract from the host cell, all using standard methods known to a skilled artisan.

Figure 5B:
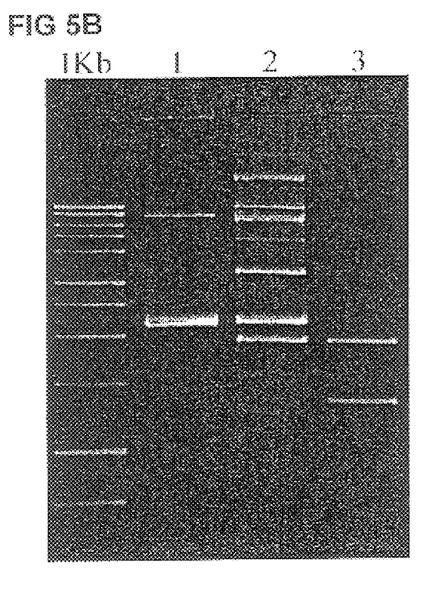
FIG. 5B depicts the transposition products obtained using a mutant transposase of the invention to catalyze transposition in vitro.

Incubation with Tnp sC7v2,0 results in conversion of 66% of supercoiled plasmid into transposition products and intermediates after a three hour incubation. In FIG. 5B, lane 1 is unreacted substrate pGT4. The transposition activity promoted by Tnp sC7v2.0 on IE$^{ME}$ transposons is shown in lane 2 Lane 3 is the result of pGT4 digestion with PvuII restriction endonuclease.

Figure 5C:
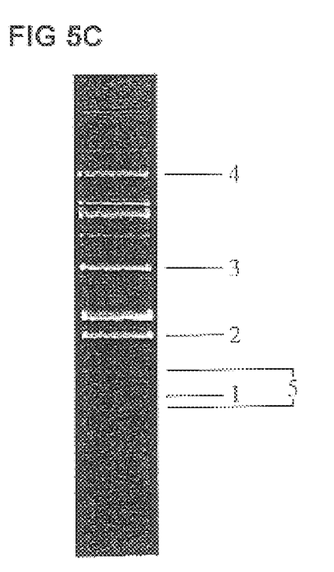
FIG. 5C further characterizes the products of lane 2 of FIG. 5B.

Though transposition reactions performed in this fashion can lead to many different DNA products, the reaction can be interpreted by analyzing certain diagnostic fragments as defined previously by Goryshin and Reznikoff (1998), suppa. FIG. 5C is a reproduction of lane 2 of FIG. 5B. Band 1 is the excised transposon. It is an intermediate that has undergone double ended break from the plasmid but has not undergone strand transfer. Band 2 is the donor backbone DNA that is released upon double-ended excision of the transposon. These bands have the same molecular weight as the products of the PvuII digest shown in lane 3 of FIG. 5B. Band 3 represents substrate plasmid that has undergone cleavage at one transposon end. It migrates at the same position as linearized plasmid (data not shown). Bands 4 and 5 are two different types of strand transfer products. Band 4 is the result of a transposon inserting intermolecularly into an unreacted plasmid. This results in a relaxed circular DNA that is longer than the original substrate plasmid by the length of the inserted transposon. The bands denoted as 5 are the result of intramolecular inversion events. These transposition products are the size of the transposon but circularized. These circularized transposition products can contain differing numbers of nodes and hence migrate in different positions on the gel.

Structure1 Function Analysis

The hyperactive Tn5 transposase mutant Tnp sC7v2.0, which increases transposition of IE$^{ME}$ flanked transposons by 7.4×10$^5$ times, includes mutations at amino acids 8, 58, 344, and 372. Analysis of Tnp sC7 revealed that the hyperactivity conferred by both the E58V and E344K mutations depends upon the transposon termini sequence. This phenotype occurring for E58V was not surprising, as previous random mutagenesis screens performed with OE flanked transposons resulted in the isolation of proteins with mutations at either amino acid 47 or amino acid 54 which had sequence specific activity (Zhou and Reznikoff, 1997; Zhou, M., Bhasin, A., and Reznikoff, W. S., "Molecular genetic analysis of transposase-end DNA sequence recognition: cooperativity of three adjacent base-pairs in specific interaction with a mutant Tn5 transposase," *J. Mol. Biol.* 276:913–925 (1997)). The sequence specific activity of a mutation at amino acid 344 that suggests that the residue also interacts with transposon end DNA, however, was indeed very surprising.

Recently a protein-DNA co-crystal representing Tnp EK/LP complexed with pre-cut (no donor backbone) OE DNA has been solved. In this complex amino acid 58 is shown to interact specifically with OE at position 10. This places the mutant residue in the vicinity of position 12, the nucleotide mutation that it was initially chosen to repress. Positions 10, 11, and 12 are all different between IE and OE and furthermore it is near one of two areas that contain major groove modification by dam methylase (position 11 of top strand and position 12 of bottom strand).

The structure further shows that amino acid 344 interacts with DNA at position 7 of OE. While position 7 is not one of the seven that distinguishes IE from OE it is between both position 4 and the region of nucleotides 10, 11, and 12 that differentiate the two. It is therefore plausible that the activity difference of Tnp E344K with IE and OE can be attributed to context effects of these two regions. We therefore propose that both mutations E58V and E344K are interacting with end sequence DNA and alter transposase function at the level of primary sequence recognition.

The leucine to glutamine mutation (L372Q), which was present in all sequenced mutants (sA5, sB2, sC6, sC7, and sD5), was both familiar and surprising. It was familiar because a hyperactive mutation at this position was previously isolated. It was surprising because the previously isolated mutation causes a leucine to proline (L372P) substitution at this position (Weinreich et al., 1994). The L372P mutation results in two consecutive proline residues in an a helix. In the co-crystal this destabilizes amino acids 372–390. It is proposed that the mutation changes the confirmation of the catalytic domain in relation to the C-terminal dimerization domain. This alteration can improve activity by increasing the distance between the N and C termini. The close proximity of these termini in Tnp WT is thought to decrease the rate of transposition of Tnp WT (Reznikoffet al., 1999). The wild-type leucine residue, visible in an earlier partial Tnp structure (Davies, D. R., Braam, L. M., Reznikoff, W. S. and Rayment, I., "The three-dimensional structure of a Tn5 transposase-related protein determined to 2.9-A resolution," *J Biol Chem.* 274: 11904–11913 (1999)), is buried in a hydrophobic pocket. It is likely that substitution with a glutamine destabilizes this hydrophobic packaging. Given that two different hyperactive mutations have been isolated by PCR-base random mutagenesis techniques that only result in single nucleotide changes in the codon and can only make five different amino acid substitutions at this residue (methionine, valine, arginine, proline, or glutamine), it is likely that a more direct mutagenesis approach such as codon randomization could reveal other interesting mutants.

The mutation R8C, which reduces OE related transposition almost 10-fold in the wild-type background (R8C 'plus one') and increases it approximately 2-fold when removed from the sC7 background (8C 'minus one') is less easy to interpret. In the co-crystallographic structure the arginine residue is not in an area of DNA contact. However this structure only represents a still picture of the complex after cleavage has occurred and it is possible that this region contacts DNA in the initial synapse.

IE Methylation

The inside end of the Tn5 transposon contains two GATC signal sequences that add four methyl groups into the major groove of each end. In this study, we were able to isolate a single mutation, E58V, which not only overcomes this binding inhibition but also appears to preferentially function on transposons in which the methyl groups are present (presumably due to increased binding affinity). Furthermore, the co-crystal structure of Tnp EK/LP complexed with pre-cleaved DNA shows that glutamate 58 interacts directly with position 10 of OE in the major groove. This region is in the vicinity of the methyl group that is present on the adenine of the non-transferred strand of IE$^{ME}$. The fact that a single amino acid change can result in this extreme change in phenotype leads us to propose that this methyl group alone is responsible for the inhibition of binding of transposase to IE$^{ME}$. The inhibition of binding by Tnp WT to IE$^{ME}$ is likely caused by an interaction between the methyl group and the negatively charged side chain of glutamate 58. Replacing the residue with a valine can not only remove an unfavorable interaction but also lead to an increase in binding affinity due to hydrophobic packaging between the side chain of the valine residue and this methyl group.

General Materials and Methods

Media and Reagents

Papillation assays were performed using glucose minimal Miller media (Miller, J., *Experiments in Molecular Genetics*, Cold Spring Harbor Laboratory Press, Cold Spring Harbor, N.Y. (1992)) supplemented with ampicillin, chlorampheracol, 5-bromo-4-chloro-3-indolyl-β-D-galactoside, and phenyl-β-D-galactoside (Trp—XG-PG plates) as described previously by Zhou, M., & Reznikoff, W. S., spra. After transformation during site directed mutagenesis, the cells were outgrown in SOC media as indicated in the altered sites protocol (Promega). All other bacterial growth was performed in Luria Broth (Sambrook, J., Fritsch, E. F. & Maniatis, T. (1989). Molecular Cloning: A Laboratory Manual, Cold Spring Harbor Laboratory Press, Cold Spring Harbor, N.Y.). When necessary, antibiotics (Sigma) were added at the following concentrations: ampicillin 100 µg/ml; chloramphenicol 20 µg/ml; nalidixic acid 20 µg/ml; gentamycin 5 µg/ml; tetracycline 15 µg/ml. Taq DNA Polymerase, T4 polymerase, T4 ligase, dNTP's, and all components of the Altered Sites Mutagenesis kit were purchased from Promega. Restriction enzymes were purchased either from Promega or New England Biolabs. Oligonucleotides used in site directed mutagenesis, sPCR, and sequencing were purchased from Research Genetics. Radionucleotides used in sequencing were from Amersham.

Construction of Plasmids

Plasmid pGT4 was constructed as a high copy number plasmid containing a kanamycin resistance gene flanked by two inside ends. It is designed so that digestion with PVUII releases the transposon from its pUC vector backbone.

The fourteen pRZ9905 (sC7) derivatives and pRZ9905 (sC7 version 2.0) were constructed by swapping restriction fragments between pRZ9905 and pRZ9905 (sC7).

Bacterial Strains

Cloning of plasmids and the directed evolution process were performed in JM1 09 (Promega). The site-directed mutagenesis protocol utilized strain ES1301 (Promega) and JM109. In the mating out assay, transposase plasmids were transformed into strain RZ212 [Δ(lac-proA,B), ara, gtr, recA56, srl, thi/pOX39-Gen], followed by conjugation into 14R525[F-na/r].

Directed Evolution Process

Directed evolution of Tn5 transposase was carried out by sPCR, basically as described previously by Stemmer (1994). Forty micro liters (~4 µg) of a pRZ9905 plasmid mini prep (Wizard SV preps, Promega) were partially digested in a 50 µl volume containing 100 nM Tris-HCl (ph=7.0), 5 nM MgCl, and 90 ng of DNase I. After a 7-minute incubation at room temperature, the reactions were stopped by adding EDTA to 10 mM. Following the addition of loading dye (Sambrook et. al, 1989) the digegted DNA was electrophoresed in a 2% NuSieve gel (FMC BioProducts) next to pGEM DNA markers (Promega). A gel slice containing DNA fragments of 200–600 bp in size as well as a second slice containing DNA fragments from 600–1000 bp in size were excised from the gel. The DNA from these two slices was purified separately by phenol chloroform extraction (Sambrook et. al, 1989). After ethanol precipitation, the DNA pellets were dried and resuspended directly into 50 µl of an assembly reaction mix. The assembly mix contained 0.2 mM dNTP's; 2.0 mM MgCl; 5 mM KCl; 10 nM Tris-HCl pH9.0 at 25C); and 0.1% TritonX-100. After addition of 0,5 uiits of Taq DNA Polymerase, the DNA was reassembled by the following thermo cycling program: 94C for 30 seconds; 50 cycles of 94C for 20 seconds, 65C for 1 minute, and 72C for 2 minutes; and cooling to 4C. A standard PCR amplification reaction using 5 µl of the assembly reaction product as a DNA template was performed for each sample (200–600 bp and 600–1000 bp) to amplify the transposase gene. This transposase-encoding fragment was digested to completion with AflII and BglII and ligated into purified AflII/BglII digested vector DNA from pRZ9905.

Ligation products were transformed into electrocompetent JM109 cells that contained plasmid pRZ9904 (IE12A/IE12A). After outgrowth the cells were plated on Trp—XG-PG plates with chloramphenicol and ampicillin selection. The plates were incubated at 32C for 14 days. At this time pRZ9905 plasmid DNA from all colonies that exhibited at least one papillae were isolated and re-transformed into the papillation assay to confirm their papillation plus phenotype. A total of 5 pRZ9905 derivatives (out of 20,000 original colonies screened) were confirmed to be papillation plus. An equal amount of all five plasmids was then used as the substrate for a second round of mutagenesis and screening. This process was repeated for a total of four rounds of screening (~20,000 colonies/round)

Ouantitative Papillation Assay

The IE12A in vivo transposition activity of Tnp WT, Tnp sA5, Tnp sB2, Tnp sC6, and Tnp sD5 were compared by a quantitative papillation assay. Competent cells of strain JM109 harboring plasmid pRZ9904 (IE12A/IE12A) were transformed with the appropriate transposase-encoding version of pRZ9905. After outgrowth, transformed cells were plated on Trp—XG-PG plates with chloramphenicol and ampicillin. The plates were grown at 32C until colonies began to appear (~18 hours). Individual colonies were then picked with sterile sticks and spotted onto a fresh plate in a 4×4 grid pattern to evenly space all colonies. One plate of 16 colonies was spotted for each protein. Plates were incubated at 32C and quantified for transposition by observing the appearance of papillae at 24-hour intervals. Data are expressed as the average number of papillae present per colony.

Mating Out Assays

Mating out assays were performed as described previously (Yin et al., 1988; Goryshin et al., 1994). Bacterial cells with the transposon containing plasmids pFMA52-187 (with either two OEs or two IEs) and the F factor pox-Gen were transformed with the appropriate transposase encoding plasmid pRZ9905. The donor used for the library screening was the strain JCMI0I [Δ(lacZX74, raps, dam-3]. All other mating out was-performed in *E. coli* strain RZ212 [Δ(lac-proA,B), ara, str, recA56, srl, thi]. The recipient strain used was 14R525[F-na/r]. A total of three assays were performed for each combination of transposase and end sequence, The values reported are the average of these three data points.

In Vitro Transposition Assays

Substrate plasmid pGT4 was isolated from DH5α cells using a qiafilter plasmid mega kit (Qiagen). Supercoiled monomer plasmid was isolated from a 1% agarose gel by use of the qiaquick gel purification kit (Qiagen). Reactions were performed at 37C under conditions determined by Reznikoff and Goryshin (1998). The concentration of pGT4 was 35.5 nM. Tnp sC7v2.0 was added to a concentration of 280 nM.

The foregoing is not intended to limit the scope of the invention. Rather the invention is understood to encompass all the variations and modifications that come within the scope of the appended claims.

We claim:

1. A mutant Tn5 transposase protein modified relative to wild-type Tn5 transposase protein, the mutant transposase differing from the wild-type protein at a position selected from the group consisting of amino acid 58 and amino acid 372 of SEQ ID NO:2, wherein the mutant Tn5 transposase protein has a preference for Tn5 inside ends over Tn5 outside ends.

2. A mutant Tn5 transposase as claimed in claim 1 comprising a valine at amino acid position 58.

3. A mutant Tn5 transposase as claimed in claim 1 comprising a mutation at amino acid position 372.

4. A mutant Tn5 transposase as claimed in claim 1 comprising a glutamine at amino acid position 372.

5. A mutant Tn5 transposase as claimed in claim 1, wherein the mutant transposase differs from the wild-type protein at amino acids 58 and 372.

6. A mutant Tn transposase as claimed in claim 1 comprising a val mine at amino acid position 58 and a glutamine at amino acid position 372.

7. A mutant Tn5 transposase as claimed in claim 1 further differing from wild-type Tn5 transposase at a position selected from amino acid 8 and amino acid 344.

8. A mutant Tn5 transposase as claimed in claim 7 wherein the amino acid at position 8 is cysteine.

9. A mutant Tn5 transposase as claimed in claim 7 wherein the amino acid at position 344 is lysine.

10. A mutant Tn5 transposase as claimed in claim 7 wherein the mutant Tn5 transposase differs from wild-type Tn5 transposase at amino acid position 8 and amino acid position 344.

11. A mutant Tn5 transposase as claimed in claim 1 comprising a cysteine at amino acid position 8 and a lysine at amino acid position 344.

12. A mutant Tn5 transposase as claimed in claim 1 comprising a cysteine at amino acid position 8, a valine at amino acid position 58, a lysine at amino acid position 344, and a glutamine at amino acid position 372.

13. A polynucleotide that encodes a transposase as claimed in claim 1.

14. A polynucleotide that encodes a transposase as claimed in claim 12.

15. A system for transposing a transposable DNA sequence in vitro, the system comprising:

the mutant Tn5 transposase modified relative to a wild-type Tn5 transposase, as claimed in claim 1;

a donor DNA molecule comprising the transposable DNA sequence, the sequence being flanked at its 5'- and 3' ends by a wild-type inside end sequence; and a target DNA molecule into which the transposable element can transpose.

16. A system as claimed in claim 15 wherein the inside end sequence is methylated.

17. A method for in vitro transposition, the method comprising the steps of:

combining a donor DNA molecule that comprises a transposable DNA sequence of interest, the DNA sequence of interest being flanked at its 5'- and 3'- ends by a wild-type Tn5 inside end sequence, with a target DNA molecule and a mutant Tn5 transposase as claimed in claim 1 in a suitable reaction buffer for a period of time sufficient for the enzyme to catalyze in vitro transposition.

* * * * *